United States Patent [19]
Bae et al.

[11] Patent Number: 6,063,431
[45] Date of Patent: May 16, 2000

[54] PRODUCTION OF ENZYME PRODUCTS AND RAW FEED MATERIALS USING GRAIN SEEDS

[76] Inventors: Hee Dong Bae, 144-5, Ji-dong, Suwon-City, Kyungki-do, Rep. of Korea; Kuo-Joan Cheng, 2015-6 Avenue South, Lethbridge, Alberta, Canada, T1J 1C2

[21] Appl. No.: 08/889,029

[22] Filed: Jul. 7, 1997

[30] Foreign Application Priority Data

Jan. 20, 1997 [KR] Rep. of Korea .......... 97-1499

[51] Int. Cl.$^7$ .......................... A23K 1/00
[52] U.S. Cl. .......... 426/635; 426/630; 426/807
[58] Field of Search .................. 426/630, 635, 426/807

[56] References Cited

U.S. PATENT DOCUMENTS

| | | | |
|---|---|---|---|
| 4,380,551 | 4/1983 | Frontczak | 426/28 |
| 4,821,455 | 4/1989 | Omente | 47/61 |

FOREIGN PATENT DOCUMENTS

| | | |
|---|---|---|
| 0 449 375 A2 | 10/1991 | European Pat. Off. . |
| 289287 | 4/1991 | Germany . |
| 2176386 | 12/1986 | United Kingdom . |
| 9605739 | 2/1996 | WIPO . |

OTHER PUBLICATIONS

Gibson et al., J. Cell Biochem., vol. 12C Suppl. Abstr. #407, 1988.
Gasztonyi et al., Nahrang, vol. 13(5), p. 411–15, 1969.
Piendl, A, Brauwissenschaft, vol. 28(6), p. 177–182, 1975.
Krishna Prasad et al., Cereal Chem., vol. 56(1) p. 43–44, 1979.
Chhipa et al., Ind. J. Agri. Res., vol. 10(4), pp. 217–22, 1976.
Boi–Hansen, Bios (Nancy), vol. 4(7–8), pp. 349–53, 1973.
Palmiano et al., Plant Physiol., vol. 52(3), p. 274–277, 1973.
Kikunaga et al., J. Sci Food Agric., vol. 56(3), pp. 355–43, 1991.
Rize, et al., Egypt. J. Food Sci., vol. 18(1–3), pp. 183–99, 1990.
Battershell et al, J. Cereal Sci, vol. 12, pp. 73–81, 1990.
Hamada, JAOCS, vol. 73(9), pp. 1143–1151, 1996.
Sushasini et al., J. Food Sci. Tech., vol. 32(2), pp. 98–103, 1995.
Gajjar et al., Applied Biochem. Biotech., vol. 49, pp. 101–112, 1994.
Battershell et al., J. Cereal Sci, vol. 12(1), p. 73–81, 1990.
Suk Shin Kim et al., Korean J Food Sci & Tech., vol. 29(1), p. 101–106, 1997.
Ohta et al., Kumamoto Joshi Daigaku Aakujutsukoyo vol. 34, p. 73–77, 1982.
Baxter, J Inst. Brew., vol. 90(4), pp. 277–81, 1984.
Hamada, J. Am. Oil Chem. Soc., vol 73(9), p. 1143–1151, 1996.
Suhasini et al., J. Food Sci Technol., vol. 32(2), p. 98–103, 1995.
Aajjar et al., Applied Biochem & Biotechnol. vol. 49(2), p. 101–112, 1994.
C.S. Piddington et al., *Gene*, 133:55–62, 1993.
Jan Pen et al., *Bio/Technology*, 11:811–814, 1993.

*Primary Examiner*—Chhaya D. Sayala
*Attorney, Agent, or Firm*—Darby & Darby

[57] ABSTRACT

This invention describes the germination technology for cereal and oil seeds for the production of enzymes and also describes the production technology of various high activity enzyme products such as phytase from the germinated seeds. The invention provides the use of germinated seeds after crushing (or pulverizing) as economically viable raw materials for mixed feeds and also provides the use of the enzyme products as filler materials for various pharmaceuticals for livestock. The production of enzyme products from seeds are achieved through four steps including selection of seeds, germination, culturing and drying, crushing and packaging.

6 Claims, 2 Drawing Sheets

PRODUCTION OF ENZYME PRODUCTS AND RAW FEED MATERIALS USING GRAIN SEEDS

BACKGROUND OF THE INVENTION

1. Field of the Invention

The present invention relates to the production of high activity enzymes using various seeds. More specifically, the present invention relates to a mass production protocol for enzymes of high activity based on the idea that when cereal and oil seed were germinated at proper environmental conditions, large quantities of enzymes of high activity could be obtained.

2. Description of the Prior Art

An enzyme is a protein which binds to a substrate and causes to enhance the utility of the substrate. It is an essential substance necessary for maintenance and activation of biological mechanisms of living entities. Based on understanding their biochemical characteristics and importance in life, enzymes have been actively utilized in food, medical and pharmaceutical industries and in the field of biotechnology. Furthermore, many research activities achieved the efficient production of enzymes. However, it faces numerous obstacles to achieve the industrialization of enzyme productions. Another problem is to develop a methodology which could maintain enzyme activities at various growth conditions (pH, temperature, etc). Thirdly, mass production technology has to be developed. In order to overcome these obstacles effectively, many attempts were made to produce enzymes utilizing a genetic engineering technology but due to their disadvantages in large scale production and lack of economic competitiveness, practical use of the technology hampered and also the success rate of the technology was not high.

SUMMARY OF THE INVENTION

An objective of the present invention is to provide a mass production method of high activity enzymes.

Another objective of the invention was aimed to utilize the raw feed materials from geminated seeds as the source of raw materials in the assorted (or mixed) feed production, thus to contribute the increased productivity of domestic animals.

A further objective of the invention was aimed to reduce environmental contamination caused by the animal's manure by reducing the quantities of organic phosphate in manure after feeding enzyme supplemented feed from germinated seeds to domestic animals.

DETAILED DESCRIPTION OF THE INVENTION

Figure 1A:
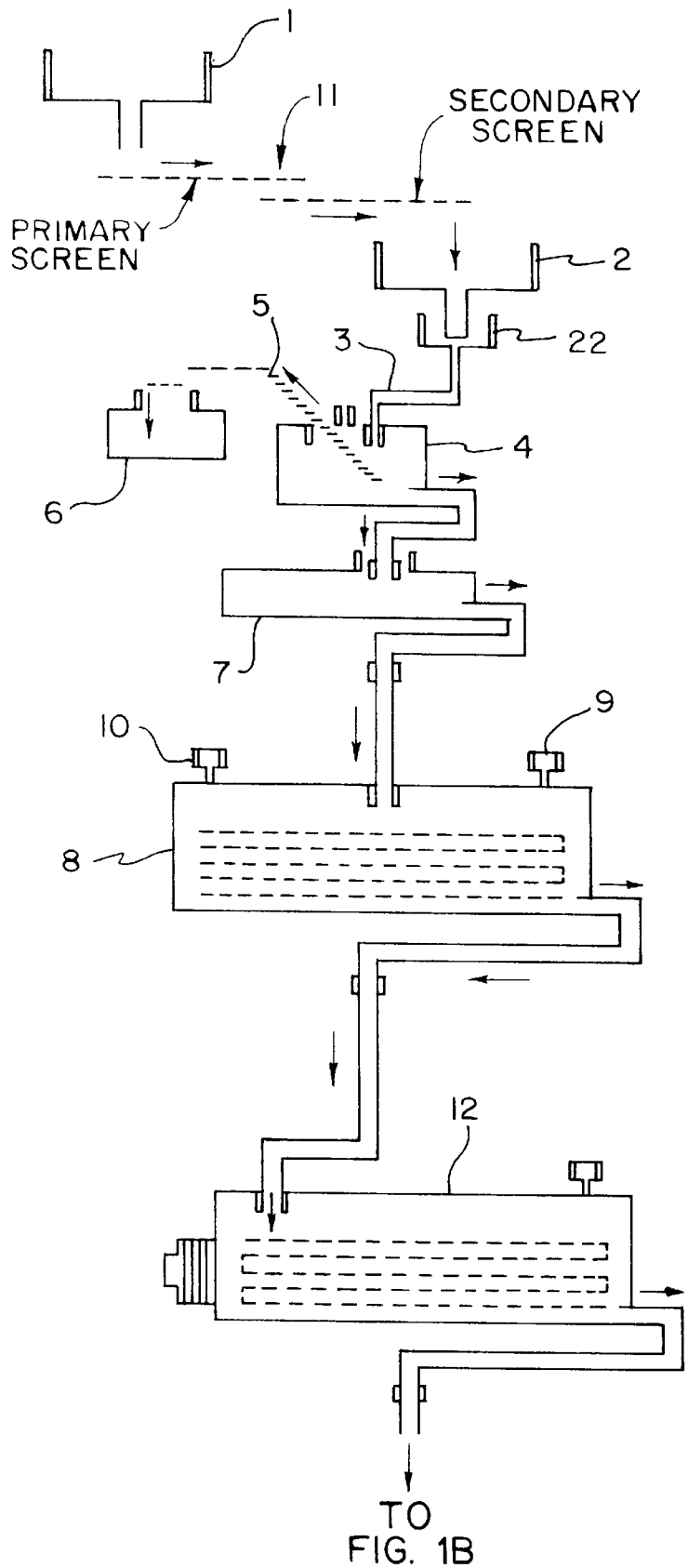
FIGS. 1A and 1B represent the bloc diagram depicting the processes of the invention.

In this invention, it was aimed to overcome difficulties faced for production of enzymes using microorganisms, and the invention was based on the fact that highest enzyme activity was observed during the germination period o various seeds.

The inventor discovered that maximum activity of amylase, cellulase, pectinase, CMCase, beta-glucanase xylanase, proteinase during the germination period of cereal and oil seeds such as barley, wheat, corn, soy bean and canola. Enhanced activity of phytase was also observed during the germination period of these seed. The invention provides enzyme production technology utilizing germination of seeds and harvesting them at optimum stage of enzyme activities. Cereal which are the source of raw materials supplying starch for animal feed contains large quantity of organic phosphate. Mono-gastric animals, such as chicken, pig and dog, lack enzymes which hydrolyse the organic phosphates in their digestive tracks. Therefore, organic phosphate cannot be digested in these animals. In order to compensate this disadvantage, inorganic phosphates are supplemented for the production of mixed feed. This causes increased cost of feed and environmental contamination due to excessive use of the inorganic phosphate. Since these animals cannot utilize organic phosphates, the use of phytase, which hydrolyze organic phosphate, in the mixed feed would contribute enhancement of feed utilization by these animals, and would maximize the productivity and reduce the cost of animal meat production and also reduce environmental contamination by organic phosphates.

Recently, based on these logic, there were many attempts to supplement phytase and other enzymes in animal feeds not only for mono-gastric animals but also for ruminants such as cattle, deer, sheep and goat. Many studies have been conducted in these area of works in the United States, Canada, Japan, the Netherlands, Germany, United Kingdom and Finland. In the Netherlands, it is compulsory to supplement phytase in animal feeds.

In those countries where high density of human population with smaller territory, with proportionally higher number of domestic animals experiences severe environmental contamination problems in rivers and grass land due to organic phosphates in animal manure because some animals could not digest them. The present invention would contribute to enhance the utilization of animal feeds, to reduce the environmental contamination, to reduce the cost of feed significantly and increase the growth rate of animals by using phytase and other enzymes from germinated grain seeds. Furthermore, in this invention, utilizing the production mechanisms of enzymes during the germination period of various plant seeds, it provides an economic and efficient enzyme production protocols. Up to date, there are no reports which describe practical utilization of the phytase through germination process of seeds.

In the invention, the enzyme production technology through germination of grain seeds was developed based on the following principles. In general, plants produce seeds for reproduction. To promote the growth of the germinated seeds effectively, particularly at the early stage of germination, various accumulated nutrients in the seeds are hydrolyzed and utilized. Seeds contain, as nutrient, starch, oils and proteins as the energy source and mineral such as phosphate which is required essentially for growth. Enzymes are required essentially to utilize effectively the accumulated nutrients in seeds. Thus, secretion of various enzymes starts when certain conditions for germination are met. At the beginning of sprout of seeds at certain environmental conditions, various enzymes hydrolyses accumulated nutrients in the seeds to provide energy and essential minerals for the growth and at the sam time various enzymes are more produced in the seeds. Especially, adenosine triphosphate (ATP), which is constituted of phosphate, is necessary for energy metabolism. The ATPs were supplied by the hydrolysis of organic phosphate by the action of phytase. Besides, beta-glucanase, proteinases and other enzymes are produced and function for the digestion of various accumulated nutrients. The quantities and activities of the produced enzymes depend on classification of seeds, germination conditions such as temperature, moisture, moisture content of seed and duration of incubation. Even seeds from the same species, for example rice seeds, the quantities and activities of enzymes differ depending upon the quantities of proteins, structural differences of starch, breeds and cultivars of seeds.

In the present invention, we identified the optimal germinating conditions of various seed and selected the best condition for enzyme production in order that the livestock and feed industries could utilize this technology effectively. In this invention, the production of phytase was priorized and the other enzymes were dealt with auxiliarily.

Figure 1B:
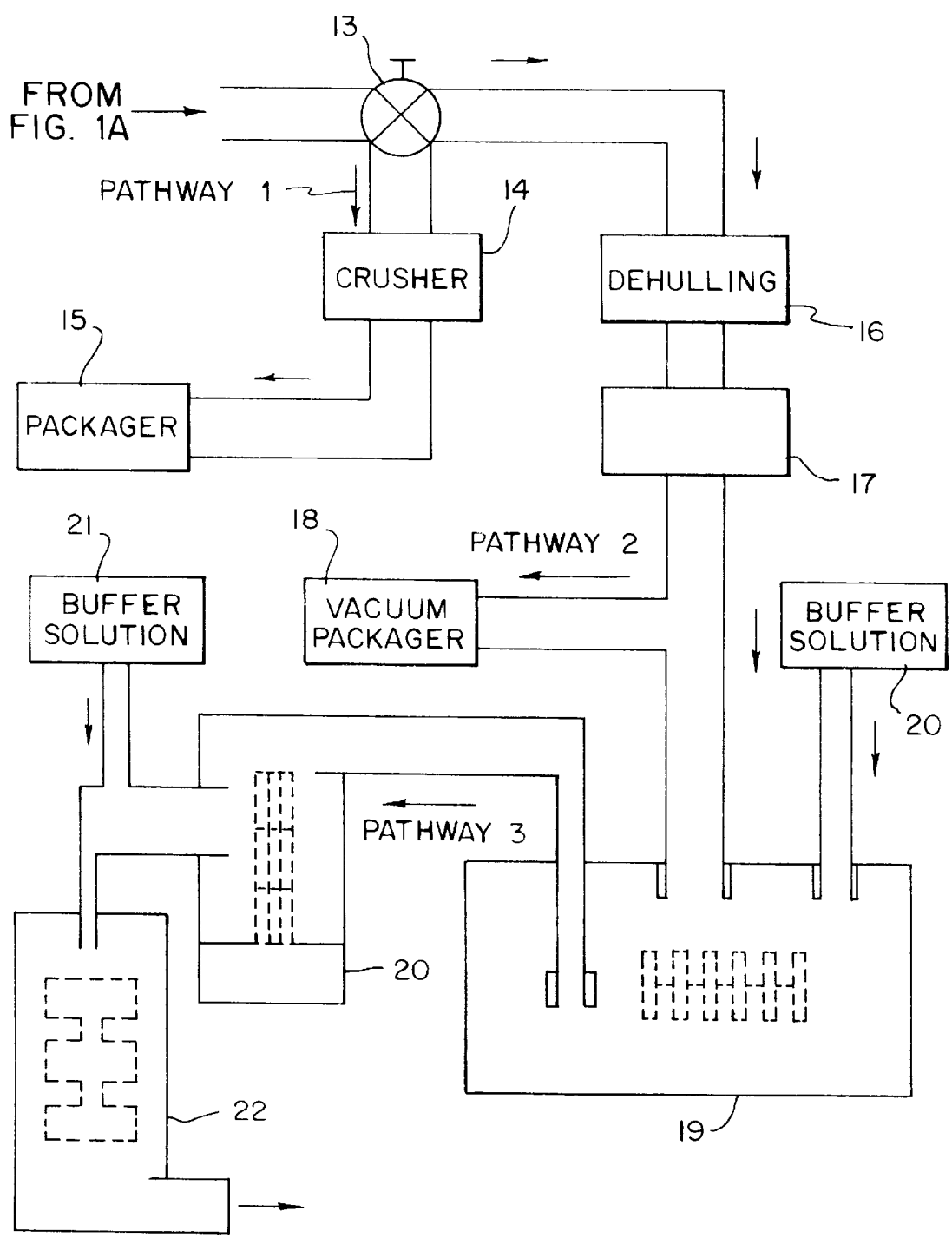

The following descriptions reveal the steps a producer could easily adapts for the processes of selection of seeds, culture, dry, crushing and packaging, with reference to FIG. 1. In this invention, production of raw feed materials were processed in phase 1, production of high purity feed materials were processed in phase 2; and production of enzyme products were processed in phase 3;

The First Process: The Process of Seed Selection

Seeds stored in the bin (1) are transported to Screen (11) and broken and damaged seeds are removed in the first screening and those seeds with retarded sprouting and fungus infested seeds are also removed in the second screening. Those seeds passed the 1st screen are placed into a salt solution and only those seeds which immerse into the solution are used. The floating seeds are discarded after collection with a collection equipment (5). The selected seeds through the 1st and 2nd screening are submerged in a vessel (7) containing non-ionic hydrophilic emulsifier and then transfer to germination incubator (8) equipped with thermometer (9) and hygrometer (10).

The Second Process: The Process of Germination and Incubation

The above selected seeds are evenly spread and incubated at proper humidity and temperature. At the time when maximum amount of enzymes are produced, the incubation are terminated and dry processes initiated.

The Third Process: The Process of Dry

At the end of 2nd process, the germinated seeds (it will be termed hereafter as "enzyme products") are harvested and subjected to dry process with a hot dry air generator (12).

The Fourth Process: The Process of Crushing and Packaging

The dried enzyme products from the 3rd process are processed into three kinds of products as illustrated in FIG. 1. The 1st products represent high purity enzyme products and processes by removing hulls using a dehulling machine (16), crushing into 0.1 mm sizes of pieces and packaging using a vacuum packager (18) (pathway #2), the 2nd products are produced to supplement animal feeds. The enzyme products with the hulls are crushed with a crusher (14) and packaged (15) (pathway #1). The 3rd products represent liquid enzyme products produced by submerging the powdered products of high purity from the pathway #1 above in the buffer solution (20)(21) and extracting enzymes using an enzyme extractor (19) and obtains supernatants after centrifugation (20) (pathway #3). These three products are stored in a dry cold room.

In the following, we describe the practical operation for the enzyme and feed production processes in details.

Practical Operation 1

After screening, barley grains were submerged in a 1.5% sodium chloride solution then transferred into water. At the moisture content of the barley at 50%, the barley grains were incubated for 30 hours at 25–30° C. maintaining a humidity of 90–95% inside the incubator. The germination process was terminated at a sprout length of 2.0 cm and heat dried at 40° C. for 36 hours. The moisture contents of the germinated and dried barley grains was 9%.

Practical Operation 2

All processes were identical with operation #1 above except the barley were submerged 12 hours in 0.05% polysorbate as a non ionic hydrophilic emulsifier in order to accelerate the speed of germination. It shortened the germination period about 12–24 hours. Moisture content of the germinated and dried barley grains was 12%.

Practical Operation #3

Except using rice seed, all processes were identical with operation #1 above. Moisture content of the germinated and dried rice seed was 9%.

Practical Operation #4

Except using wheat, all processes were identical with operation #1 above. Moisture content of the germinated and dried wheat seed was 9%.

Practical Operation #5

Soy beans after screening were submerged into 3.0% sodium chloride solution. At moisture content of 60% of the beans, the beans were incubated for 36 hours at 30° C. with a humidity inside the incubator ranging 90–95% at the sprout length 1 cm, the incubation was terminated and the beans were subjected to dry heat for 24 hours at a temperature of 80° C. of a hot air drier. Moisture content of the products was 12%.

Practical Operation #6

Except using canola seed, all processes were identical with operation #5 above. Moisture content of the germinated and dried canola was 9%.

Practical Operation #7

All processes were identical with operation #5 above except the beans were submerged for 4 hours in 10% polysorbate 80, as a non-ionic hydrophilic emulsifier, in order to accelerate the speed of germination. It shortened the germination period about 24–36 hours. Moisture content of the final products was 12%.

Practical Operation #8

All processes were identical with operation #5 above except corns were used. The lengths of corn sprouts were 1.5 cm and the final products has a moisture content of 10%.

To stabilize enzyme activity from enzyme extracts obtained from crushed enzyme products, the liquid enzyme extracts were received $MgCl_2$ at a concentration of 0.5–1.0M. Liquid enzyme products were obtained after centrifuging these enzyme products at 5,000 xg. A biological buffer solution was used to extract enzymes.

Experiment #1

In order to assure the stability of enzyme activity, liquid enzyme products were treated with 0.5–1.0M $MgCl_2$, $CaCl_2$ and CoCl$_2$. The effect of enzyme stability by MgCl$_2$ was resulted in more than 200 times than that of Cacl$_2$ and made possible the storage of the liquid enzyme products more than 4 months.

Experiment #2

To determine the activity of amylase extracted from germinated barley base on the invention, in vitro experiments were conducted. The quantities of glucose released from substrates such as corn, wheat and barley were 223.8 $\mu$M, 288.8 $\mu$M and 318.9 $\mu$M, respectively. In these experiments, as substrates, non-germinated corn, wheat and barley were crushed into a small particles so as to pass a sieve of 0.5 mm mesh and incubated at 38° C. for 24 hours.

Experiment #3

To determine the activity of phytase extracted from germinated barley based on the invention, in vitro experiments were conducted as experiment #2 above. From the above substrates, the quantities of released phosphate from corn, wheat and barley were 613.7 $\mu$g, 373.9 $\mu$g and 1,573.8 $\mu$g, respectively.

Experiment #4

Table 1 shows the comparative data of the amylase activities from non-germinated and germinated cereal and oil seeds based on the invention. The increases of amylase activities ranged a minimum value of 210% in wheat and soy beans and a maximum value of 1,300% in corns.

TABLE 1

Amylase activity of non-germinated and germinated cereal and oil seed

| | Amylase Activity (unit/kg) | | Relative |
| --- | --- | --- | --- |
| Cereal | Non-germinated | Germinated | Increase (%) |
| Corn | 5,200 | 66,100 | 1,300 |
| Wheat | 66,500 | 139,400 | 210 |
| Barley | 64,444 | 176,100 | 280 |
| Rice | 12,962 | 117,800 | 910 |
| Soybean | 65,679 | 133,500 | 210 |

Experiment 5

Table 2 shows the comparative data of the phytase activity from non-germinated and germinated cereal and oil seeds based on the invention. The increases of amylase activities ranged a minimum value of 120% in soy bean and a maximum value of 470% in corn.

TABLE 2

Phytase Activity of Non-germinated and Germinated Cereal and Oil Seeds

| | Phytase Activity (unit/kg) | | Relative |
| --- | --- | --- | --- |
| Cereal | Non-germinated | Germinated | Increase (%) |
| Corn | 13,900 | 64,600 | 470 |
| Wheat | 112,400 | 227,600 | 210 |
| Barley | 119,400 | 305,600 | 260 |
| Rice | 5,200 | 31,900 | 630 |
| Soybean | 39,000 | 43,900 | 120 |

Experiment 6

To determine the activities of various enzymes extracted from germinated barley, experiments were conducted as described in experiment 4 above using non-germinated barley asa control. Comparing the non-germinated barley, the activities of various enzymes have been increased in the germinated barley such as cellulase 300%, pectinase 500%, CMCase 500%, hemicellulase 300%, and protease 400%, respectively.

Experiment 7

Using soy bean, experiments identical with the experiment 6 above were conducted. Comparing non-germinated soy bean, the activities of various enzymes have been increased in the germinated soy bean such as amylase 2,500%, cellulase 400%, pectinase 600%, CMCase 500%, hemicellulase 200%, protease 600% and phytase 450%, respectively.

Animal Feed Experiment 1: Pigs

Pigs were fed the crushed enzyme products produced from barley described in the operation #1 above as the raw starch feed materials, at three months after feeding relative body weight increases of 20% were observed compared to the control group which fed with a general purpose feed.

Composition of Feeds

Starch feed (raw feed materials from the invention) 40–50%
Cellulase feed 20%
Protein feed 20%
Filler materials, pharmaceuticals and minerals 10–20%

Animal Feed Experiment 2: Broiler Chicken

Broiler chicken were fed the crushed enzyme products produced from soy beans described in the operation #5 with the same composition of feeds described above except crushed enzyme products from soy beans were used as the source of protein feed. At 8 weeks after feeding, a relative body weight increase of 15% were observed compared to the control group which fed a general purpose feed.

Animal Feed Experiment 3, Egg Laying Hens

Identical experiments described in the animal feed experiment 2 above were conducted except using egg laying hens. The relative rates of egg productions were improved 8–10% compared to the control group which fed a general purpose feed. The initial egg-laying time was shortened about 2 weeks.

Animal Feed Experiments 4: Dogs, Mink and Foxes

Identical experiments described in the animal feed experiment 2 above were conducted in dogs, mink and foxes. The relative body weight increases of 15%, 13% and 20% were observed in the dogs, mink and foxes, respectively. It appears the mink and foxes belong to the treated groups have glossier skins than control animals. Enzyme products from germinated grain seeds contains high quantities of various high activity enzymes, therefore, various substrates are expected to be synergistically hydrolysed. We confirmed an excellent replacement effect by supplementing 0.5%(w/w) enzyme products in animal pharmaceuticals compared to the filler materials.

Effect of the Invention

In this invention, an enzyme production technology was developed from germinated grain seeds. The technology utilizes the natural law, and produces maximum amounts of enzymes at low cost. The enzyme products are safe without toxicity for animal use since the products were produced from grains which are consumed by human and animals. The enzyme products contain not only maximum amount of phytase but also large quantities of the enzyme; various substrates are expected to be synergistically hydrolysed. The enzyme products demonstrated an excellent replacement effect since the enzyme products contain various nutrients as raw feed materials for the production of mixed feeds compared to other raw feed materials.

By using the enzyme products, it is not necessary to supplement phytase in feeds for ruminants and animals with a single stomach for the digestion of organic phosphates. Therefore, it proves the present invention is very useful in the animal feed and livestock industries since its use is advantageous economically by reducing the cost of feeds significantly.

What is claimed is:

1. An isolated multi-enzyme product containing phytase, obtained by germinating seeds from barley, rye, oat or canola.

2. A method of producing a multi-enzyme containing product including a phytase with enhanced enzyme activity, comprising:

a. immersing the seeds in sodium chloride solution and discarding inferior seeds;

b. adjusting the moisture content of the seeds to 40–60%;

c. incubating the seeds at 25–30° C. for 24–36 hours at a humidity of 90–95% to form germinated seeds;

d. hot air drying the seeds to reduce the moisture content of the seeds to 9–12%; and e. crushing the dried germinated seeds, thereby producing said multi-enzyme containing product including phytase having an enzyme activity 120% greater than phytase from non-germinated seeds.

3. The method of claim 2, further comprising extracting multiple enzymes from the crushed germinated seeds by a buffer solution containing 0.5–1.0M $MgCl_2$ to maintain the stability of the multiple enzymes.

4. The method of claim 2, further comprising submerging the seeds for 4–12 hours into 0.05–10.0% polysorbate 80 as a non-ionic hydrophilic emulsifier to accelerate the speed of germination.

5. A method of supplementing the diet of livestock, comprising feeding the multi-enzyme containing product produced by the method of claim 2 to livestock.

6. The method of claim 3, further comprising centrifugation of the extract to produce a liquid multi-enzyme product.

* * * * *